US011386556B2

(12) United States Patent
Saget et al.

(10) Patent No.: US 11,386,556 B2
(45) Date of Patent: *Jul. 12, 2022

(54) DEFORMED GRID BASED INTRA-OPERATIVE SYSTEM AND METHOD OF USE

(71) Applicant: Orthogrid Systems Inc., Salt Lake City, UT (US)

(72) Inventors: Edouard Saget, Salt Lake City, UT (US); Richard Boddington, Salt Lake City, UT (US)

(73) Assignee: Orthogrid Systems Holdings, LLC, Salt Lake City, UT (US)

( * ) Notice: Subject to any disclaimer, the term of this patent is extended or adjusted under 35 U.S.C. 154(b) by 236 days.

This patent is subject to a terminal disclaimer.

(21) Appl. No.: 16/821,447

(22) Filed: Mar. 17, 2020

(65) Prior Publication Data
US 2020/0219258 A1 Jul. 9, 2020

Related U.S. Application Data

(63) Continuation-in-part of application No. 16/216,090, filed on Dec. 11, 2018, now Pat. No. 10,991,070, (Continued)

(51) Int. Cl.
*G06K 9/00* (2022.01)
*G06T 7/00* (2017.01)
(Continued)

(52) U.S. Cl.
CPC .......... *G06T 7/0012* (2013.01); *A61B 6/4225* (2013.01); *A61B 6/4291* (2013.01);
(Continued)

(58) Field of Classification Search
CPC ......... G06T 7/0012; G06T 7/337; G06T 7/38; G06T 7/80; G06T 19/006;
(Continued)

(56) References Cited

U.S. PATENT DOCUMENTS 5,052,035 A    9/1991  Krupnick
6,118,845 A *  9/2000  Simon ................. A61B 6/5252
                                                     378/207

(Continued)

OTHER PUBLICATIONS

Lin et al. Three-dimensional computer-assisted surgical simulation and inoperative navigation in Orthognathic Surgery: A Literature Review. In J of the Formosan Med. Asso. (2015).
(Continued)

*Primary Examiner* — Solomon G Bezuayehu
(74) *Attorney, Agent, or Firm* — Veritay Group IP, PLLC; Susan B. Fentress; Liam O'Donnell (57) ABSTRACT

The subject of this invention is a system and method for distortion adaptation for use with an imaging grid alignment apparatus (analogue or digital) and method of intra-operative use for joint replacements, spine, trauma fracture reductions and deformity correction and implant placement/alignment. The system provides for real time dynamic position tracked distortion-adaption grid.

11 Claims, 10 Drawing Sheets

Related U.S. Application Data which is a continuation-in-part of application No. 15/383,975, filed on Dec. 19, 2016, now Pat. No. 10,201,320.

(60) Provisional application No. 62/357,293, filed on Jun. 30, 2016, provisional application No. 62/269,698, filed on Dec. 18, 2015.

(51) Int. Cl.

| | | |
|---|---|---|
| *A61B 6/00* | (2006.01) | |
| *G06T 7/80* | (2017.01) | |
| *G06T 7/33* | (2017.01) | |
| *G06T 7/38* | (2017.01) | |
| *G06T 19/00* | (2011.01) | |
| *A61B 90/00* | (2016.01) | |
| *G16H 30/20* | (2018.01) | |
| *G16H 30/40* | (2018.01) | |

(52) U.S. Cl.
CPC ............ *A61B 6/4441* (2013.01); *A61B 90/37* (2016.02); *G06T 7/337* (2017.01); *G06T 7/38* (2017.01); *G06T 7/80* (2017.01); *G06T 19/006* (2013.01); *G16H 30/20* (2018.01); *G16H 30/40* (2018.01); *A61B 2090/376* (2016.02); *G06T 2207/30012* (2013.01); *G06T 2207/30052* (2013.01); *G06T 2210/41* (2013.01)

(58) Field of Classification Search
CPC . G06T 2207/30012; G06T 2207/30052; G06T 2210/41; A61B 6/4225; A61B 6/4291; A61B 6/4441; A61B 90/37; A61B 2090/376; A61B 6/466; A61B 6/487; A61B 6/582; A61B 2017/00725; A61B 2090/365; G16H 30/20; G16H 30/40
See application file for complete search history.

(56) References Cited

U.S. PATENT DOCUMENTS

| | | | |
|---|---|---|---|
| 6,269,177 B1 | 7/2001 | Dewaele et al. | |
| 6,438,401 B1 | 8/2002 | Cheng et al. | |
| 6,445,182 B1* | 9/2002 | Dean ................ | G01R 33/4822 |
| | | | 324/309 |
| 6,470,207 B1* | 10/2002 | Simon ................ | A61B 6/547 |
| | | | 378/207 |
| 6,711,432 B1 | 3/2004 | Krause et al. | |
| 7,394,946 B2 | 7/2008 | Dewaele | |
| 7,493,153 B2 | 2/2009 | Ahmed et al. | |
| 7,664,289 B2 | 2/2010 | Worthington et al. | |
| 7,664,298 B2 | 2/2010 | Lang et al. | |
| 7,676,023 B2* | 3/2010 | Lang ................ | G06T 7/0012 |
| | | | 378/54 |
| 7,764,293 B2 | 7/2010 | Kakuta et al. | |
| 7,852,355 B2 | 12/2010 | Friedrich et al. | |
| 7,935,048 B2 | 5/2011 | Yaron et al. | |
| 8,194,936 B2 | 6/2012 | Abramoff et al. | |
| 8,300,764 B2 | 10/2012 | Yamaguchi | |
| 8,484,001 B2 | 7/2013 | Glozman et al. | |
| 8,532,352 B2 | 9/2013 | Ionasec et al. | |
| 8,554,697 B2 | 10/2013 | Claus et al. | |
| 8,611,697 B2 | 12/2013 | Nathaniel et al. | |
| 8,698,843 B2 | 4/2014 | Tseng | |
| 8,810,599 B1 | 8/2014 | Tseng | |
| 8,831,324 B2 | 9/2014 | Penenberg | |
| 8,855,389 B1 | 10/2014 | Hoffmann et al. | |
| 8,890,896 B1 | 11/2014 | Tseng | |
| 9,042,621 B2 | 5/2015 | Ashby et al. | |
| 9,064,332 B2 | 6/2015 | Valadez et al. | |
| 9,109,998 B2 | 8/2015 | Nathaniel et al. | |
| 9,111,180 B2 | 8/2015 | Rappaport et al. | |
| 9,153,195 B2 | 10/2015 | Geisner et al. | |
| 9,213,405 B2 | 12/2015 | Perez et al. | |
| 9,277,970 B2 | 3/2016 | Mansi et al. | |
| 9,430,496 B2 | 8/2016 | Tseng | |
| 9,433,390 B2 | 9/2016 | Nathaniel et al. | |
| 9,437,036 B2 | 9/2016 | Yoo et al. | |
| 9,456,874 B2 | 10/2016 | Kubiak et al. | |
| 9,529,424 B2 | 12/2016 | Hilliges et al. | |
| 9,538,962 B1 | 1/2017 | Hannaford et al. | |
| 9,560,291 B2 | 1/2017 | Weiser et al. | |
| 9,610,134 B2 | 4/2017 | Kubiak et al. | |
| 9,737,369 B2 | 8/2017 | Burger et al. | |
| 9,754,371 B2 | 9/2017 | Kateb et al. | |
| 9,821,174 B1* | 11/2017 | Fram ................ | G16H 40/63 |
| 9,936,879 B2* | 4/2018 | Piron ................ | A61B 34/30 |
| 10,092,164 B2 | 10/2018 | Sholev et al. | |
| 10,092,362 B2 | 10/2018 | Wasielewski et al. | |
| 2004/0044295 A1 | 3/2004 | Reinert et al. | |
| 2004/0152970 A1* | 8/2004 | Hunter ................ | A61F 2/4425 |
| | | | 600/424 |
| 2004/0152972 A1* | 8/2004 | Hunter ................ | G16Z 99/00 |
| | | | 128/899 |
| 2004/0215071 A1* | 10/2004 | Frank ................ | A61B 6/463 |
| | | | 600/407 |
| 2005/0085718 A1* | 4/2005 | Shahidi ................ | A61B 8/4245 |
| | | | 600/443 |
| 2005/0113846 A1 | 5/2005 | Carson | |
| 2006/0111631 A1 | 5/2006 | Kelliher et al. | |
| 2006/0142739 A1 | 6/2006 | DiSilestro et al. | |
| 2006/0184006 A1* | 8/2006 | Chen ................ | A61B 90/36 |
| | | | 600/416 |
| 2007/0233267 A1 | 10/2007 | Amirouche et al. | |
| 2007/0238952 A1* | 10/2007 | Boese ................ | G06T 7/55 |
| | | | 600/407 |
| 2008/0021299 A1* | 1/2008 | Meulink ................ | A61F 2/46 |
| | | | 600/407 |
| 2008/0114267 A1* | 5/2008 | Lloyd ................ | A61B 34/20 |
| | | | 606/1 |
| 2008/0123910 A1 | 5/2008 | Zhu | |
| 2008/0161684 A1* | 7/2008 | Li ................ | A61B 6/12 |
| | | | 600/417 |
| 2008/0200926 A1 | 8/2008 | Verard et al. | |
| 2009/0017430 A1 | 1/2009 | Muller-Daniels et al. | |
| 2009/0093702 A1 | 4/2009 | Vollmer et al. | |
| 2009/0099862 A1 | 4/2009 | Fireman et al. | |
| 2009/0274350 A1 | 11/2009 | Pavlovskaia et al. | |
| 2009/0281417 A1* | 11/2009 | Hartmann ................ | A61B 34/20 |
| | | | 600/424 |
| 2010/0130871 A1 | 5/2010 | Frykman et al. | |
| 2011/0152676 A1 | 6/2011 | Groszmann et al. | |
| 2012/0123422 A1 | 5/2012 | Agnihotri et al. | |
| 2012/0230566 A1* | 9/2012 | Dean ................ | A61F 2/30942 |
| | | | 382/128 |
| 2013/0113802 A1 | 5/2013 | Weersink et al. | |
| 2013/0294667 A1* | 11/2013 | Zheng ................ | G06T 7/00 |
| | | | 382/131 |
| 2014/0039510 A1* | 2/2014 | van Saarloos ......... | A61B 3/107 |
| | | | 606/107 |
| 2014/0336671 A1* | 11/2014 | Panchanadikar .. | A61B 17/1703 |
| | | | 606/130 |
| 2014/0378828 A1* | 12/2014 | Penenberg ............ | A61B 6/468 |
| | | | 600/424 |
| 2015/0086955 A1 | 3/2015 | Poniatowski et al. | |
| 2015/0150460 A1 | 6/2015 | Krishnaswamy et al. | |
| 2015/0160322 A1 | 6/2015 | Matthews | |
| 2015/0238271 A1* | 8/2015 | Wollowick ........... | A61B 6/5235 |
| | | | 382/128 |
| 2015/0366628 A1 | 12/2015 | Ingmanson | |
| 2016/0191887 A1 | 6/2016 | Casas | |
| 2017/0071673 A1* | 3/2017 | Ferro ................ | G06T 19/006 |
| 2017/0105601 A1 | 4/2017 | Pheiffer et al. | |
| 2017/0105802 A1 | 4/2017 | Taraschi et al. | |
| 2017/0231714 A1* | 8/2017 | Kosmecki ............ | A61B 90/37 |
| | | | 345/419 |
| 2018/0000339 A1* | 1/2018 | Hipsley ................ | G16H 20/40 |

(56) References Cited

U.S. PATENT DOCUMENTS

2018/0233222 A1    8/2018   Daley et al.
2018/0303552 A1   10/2018   Ryan et al.

OTHER PUBLICATIONS

PCT/US2016/040173 Written Opinion dated Oct. 31, 2017.

* cited by examiner

DEFORMED GRID BASED INTRA-OPERATIVE SYSTEM AND METHOD OF USE

CROSS-REFERENCE TO RELATED APPLICATIONS

This application is a continuation in part of US patent application Ser. No. 16/216,090 now U.S. Pat. No. 10,991,070 and claims the benefit of U.S. patent application Ser. No. 15/383,975 now U.S. Pat. No. 10,201,320, and provisional patent application No. 62/730,112 filed Sep. 12, 2018 provisional patent application No. 62/269,698 filed Dec. 18, 2015 and US provisional patent application No. 62/357,293 filed Jun. 30, 2016, under 35 U.S.C. Sec. 119(e) (hereby incorporated by reference in their entirety).

STATEMENT REGARDING FEDERALLY SPONSORED RESEARCH OR DEVELOPMENT

None.

The names of the parties to a joint research agreement. Orthogrid Systems, S.A.R.L., Richard Boddington and MediLux Capital Holdings, S.A.R.L.

Reference to a "Sequence Listing," a table, or a computer program listing appendix submitted on a compact disc and an incorporation-by-reference of the material on the compact disc: None.

FIELD OF THE INVENTION

The subject of this invention is a system for distortion adaptation for use with radiographic grid alignment apparatus (analogue or digital) and method of intra-operative use for joint replacements, spine, trauma fracture reductions and deformity correction and implant placement/alignment.

BACKGROUND OF THE INVENTION

Many of the radiographic parameters essential to total hip arthroplasty (THA) component performance, such as wear, and stability, can be assessed intraoperatively with fluoroscopy. However even with intraoperative fluoroscopic guidance, the placement of an implant or the reduction of a bone fragment may still not be as close as desired by the surgeon. For example, mal positioning of the acetabular component during hip arthroplasty can lead to problems. For the acetabular implant to be inserted in the proper position relative to the pelvis during hip arthroplasty requires that the surgeon know the position of the patient's pelvis during surgery. Unfortunately, the position of the patient's pelvis varies widely during surgery and from patient to patient. During trauma surgery, proper fracture management, especially in the case of an intra articular fracture, requires a surgeon to reduce the bone fragment optimally with respect to the original anatomy in order to: provide the anatomical with joint the best chance to rehabilitate properly; minimize further long term damage and, if possible, to regain its normal function. Unfortunately, in a fracture scenario, the original anatomical position of these bone fragments has been compromised and their natural relationship with the correct anatomy is uncertain and requires the surgeon to use his/her best judgment in order to promote a successful repair and subsequent positive outcome.

Various devices are known to reduce mal positioning of these surgical components. For example, a transverse acetabular ligament has been suggested as a qualitative marker of the orientation of the acetabulum. (Archbold H A, et al. The Transverse Acetabular Ligament; an Aid to Orientation of the Acetabular Component During Primary Total Hip Replacement: A Preliminary Study of 200 Cases Investigating Postoperative Stability, J Bone Joint Surg BR. 2006 July; 88(7):883-7). However, it has been suggested that the acetabulum may be deteriorated due to arthritis. Others have proposed using a tripod device that uses the anatomy of the ipsilateral hemi pelvis as the guide to position the prosthetic acetabular component. U.S. Patent Publication Number 20090306679. This instrument has three points. The first leg is positioned in the area of the posterior inferior acetabulum, a second leg is positioned in the area of the anterior superior iliac spine and a third leg is positioned on the ileum of the subject. U.S. Patent Publication Number 20090306679. Regarding fracture fixation, or a correction of a deformity or malunion, various devices have also been suggested to support proper reconstruction-reduction of bone fragments. For example, a distal radius volar fixation plate has been suggested to act as an invasive, intraoperative quantitative supporting buttress to fix and provide a reference to the surgeon in order to help realign the broken bony anatomy.

Distortion in a radiographic image, particularly fluoroscopic images, is a well-known phenomenon (Jareš V. *The effect of electron optics on the properties of the x-ray image intensifier. Adv Electron Elect Phys.* Oct. 9, 1985; 64(8): 549-59). Several distortion correction techniques have been published to date, for example by Kedgely A E, et al. in *J Appl Clin Med Phys.* 2012 Jan. 5; 13(1):3441. doi: 10.1120/jacmp.v13i1.3441. *Image intensifier distortion correction for fluoroscopic RSA: the need for independent accuracy assessment.* These methods attempt to correct the distortion using a series of beads to calibrate the amount of distortion in an image and then attempt to correct that distortion to a non-distorted view of the image. A need exists in the industry to allow for intraoperative live adaptation of a grid (analogue, virtual, augmented, hologram, or 3D shape model) for use in measurements, positioning of implants, and alignment of anatomy and to provide distortion adaptation with a radiographic grid alignment device.

SUMMARY OF THE INVENTION

The present subject matter includes a distorted dimensioned grid alignment device made from a distortion calibration array, wherein the visualization of the dimensioned grid is deformed to accurately match the quantitative warp amount within an anatomical medical image. The present subject matter includes a method to correct for distortion of an anatomical image captured from an imaging system by registering an anatomical image to a dimensioned grid by selecting at least one anatomical landmark to provide a dimensioned grid with at least one grid indicator; calibrating the dimensioned grid to the image of a patient's anatomy to provide a calibrated dimensioned grid; and deforming the calibrated dimensioned grid to correct for the distortion of the anatomical image to generate a deformed calibrated dimensioned grid image. The method further includes the step of intra-operatively computing a point of interest in the image of a patient's anatomy with reference to the deformed calibrated dimensioned grid.

Another aspect of the present subject matter involves: a grid based intraoperative system made of a non-transitory computer-readable storage medium encoded with computer-readable instructions which form the application software and a processor to process the instructions, wherein the application software includes: a data capture module configured to capture and store a digital image acquired by an imaging device; a grid registration module configured to register an anatomical image to the grid; a distortion adaptation module configured to adapt the grid to correct for the distortion in the anatomical image; and an outcome module configured to provide at least one visual and/or auditory instruction intraoperatively to a user. The data capture module can be configured to obtain data from a sensor. The sensor can be in electronic communication with an augmented or mixed reality grid or trackable. The outcome module in one embodiment of the invention can be an augmented reality display and the outcome module can be a 3D shape model or holographic display.

BRIEF DESCRIPTION OF THE SEVERAL VIEWS OF THE DRAWINGS

The drawings show schematically a fluoroscopic alignment plate apparatus and method of use according to an example form of the present invention. The invention description refers to the accompanying drawings.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions and are not restrictive of the invention as claimed. Unless defined otherwise, all technical and scientific terms used herein have the same meaning as commonly understood by one of ordinary skill in the art to which this invention belongs.

The present disclosure begins with acquiring radiographic images, such as an X-ray images, of a patient during a surgical procedure. Digital X-ray images are acquired intraoperatively, during surgical procedures, such as joint replacements, and trauma fracture reductions and deformity correction and implant placement/alignment. The acquired image can be viewed or further processed on a display device. A grid alignment device (analogue or digital) can be used with digital radiographic, ultrasound, CT, or other imaging system images acquired intra-operatively to facilitate alignment or placement of an implant during a surgical procedure.

One of the objectives of the current technology is to provide distortion adaptation process to allow the interoperative use of digital images. When a surgeon is performing an operation, a grid based intra-operative system can operate in an intra-operative mode, whereby the surgeon can make use of the system, as a guide for adjusting the placement of an implant in the patient or the correction of a deformity. The dimensioned grid is used to define alignment parameters of anatomy and implant placement in a patient. In its simplest form, the grid can be digitally displayed over the anatomy and the surgeon can visually determine alignment and positioning measurements. However, to correct for distortion in an anatomical image, an alignment grid of geometrical shapes or lines similar to or matching certain anatomical features in specific regions of interest in an anatomical image is used to establish a distortion adaptation of the grid alignment apparatus. By this method, the anatomy is aligned intra-operatively, with the distorted anatomical geometrical grid, in any musculoskeletal application, which allows for real time intra-operative placement of implants relative to anatomy as guided by the distorted grid alignment device.

In an exemplary embodiment, a dimensioned grid is secured within the pathway of the radiographic beam (such as attached to the image intensifier). The anatomical image may or may not have distortion, but regardless of the amount of distortion present in the image, the dimensioned grid will be distorted relative to the amount of distortion present in the image, thereby providing visual quantitative analysis possible on an distorted anatomical image with the distortion-adapted dimensioned grid properly overlaid upon diverse point of interests of the anatomical image.

The process allows for the acquisition of a pre-operative or intra-operative initial image and that are subjected to a transformation process, such as for example Affine Transformation, thereby adjusting the anatomical points to rotation, translation, and scaling. Then using another processic transformation, such as B-spline metric of fit, the grid lines of the dimensioned grid are adapted real-time intra-operatively to fit the anatomy, thus producing distorted lines curving to match or fit the musculoskeletal anatomy or shape of the implant or trauma.

Figure 1:
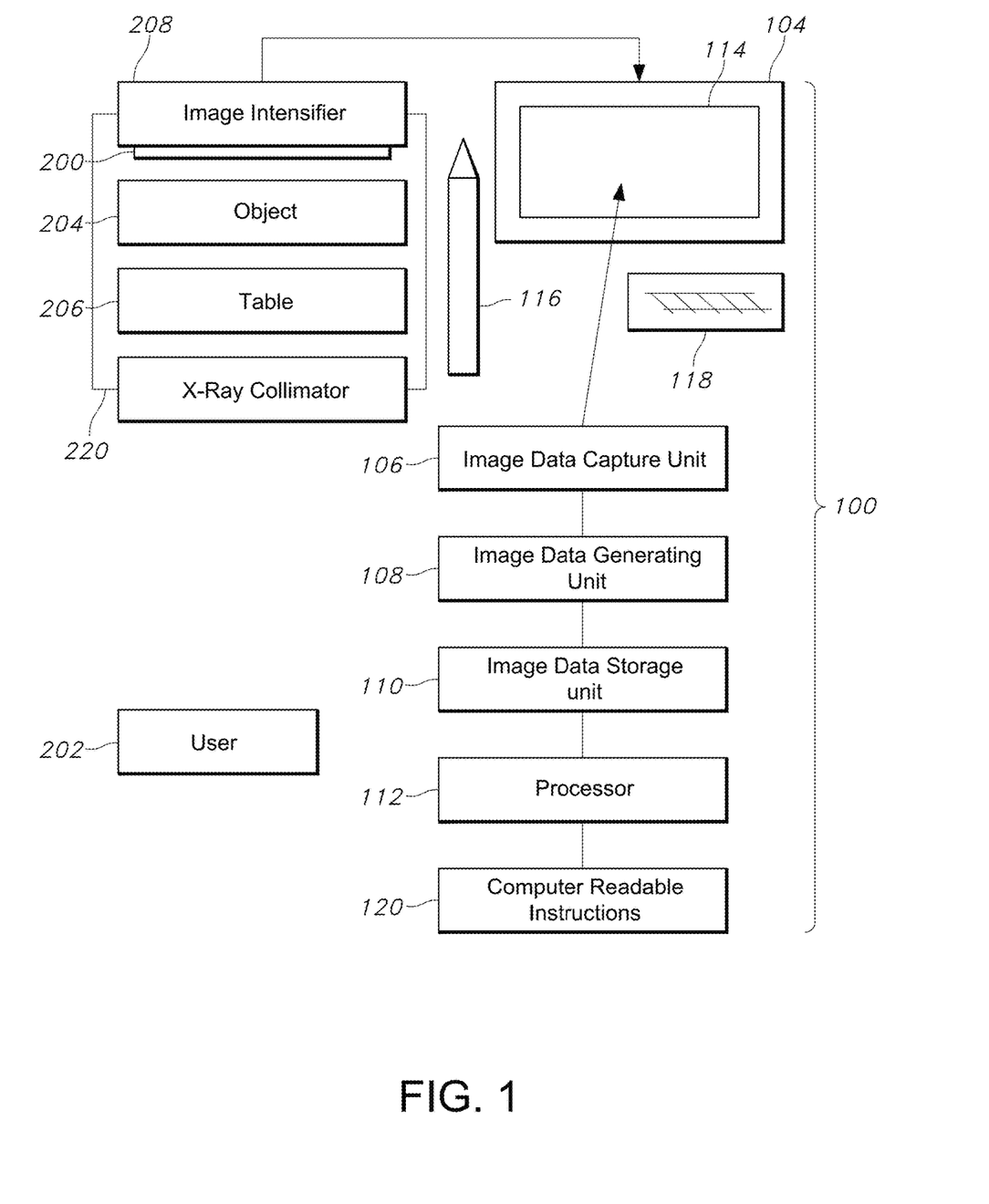
FIG. 1 shows a schematic over-view of an intraoperative deformed grid system.

Turning to FIG. 1, a grid or a distortion calibration array based intraoperative system 100 for providing a distorted dimensioned grid, such as lines curving to match or fit the musculoskeletal anatomy or the shape of the implant, as shown in distorted intra-operative images, is provided. The grid or distortion calibration array based intraoperative system 100 includes a computer workstation 104. The computer workstation 104 is made of: an image data capture unit 106; an image data generating unit 108; a non-transitory computer-readable image data storage medium 110; a processor 112; and computer-readable instructions 120. The non-transitory computer-readable storage medium 110 is encoded with computer-readable instructions, which form the application software 120. The computer workstation 104 also includes an input device 118 such as, a keyboard and a display 114, such as a monitor. The grid distortion calibration array based intraoperative system 100 can optionally include a motion-tracking device 116. In an exemplary embodiment, an image capture unit 106; an image data generating unit 108 include measurements and data can be acquired and displayed on AR/Holo lenses, glasses, or heads-up display.

The computer workstation 104 is electronically connected to an imaging system 220, such as for example C-arm and flat plate. An object, such as a patient 204 is positioned on a table 206 within the imaging system 220. A distortion calibration array 200, such an analogue embodiment, is attached to an image intensifier 208 of the imaging system 220. In another embodiment, the dimensioned grid 200 allows the application software 120 to generate a digital representation of the dimensioned grid.

Figure 2:
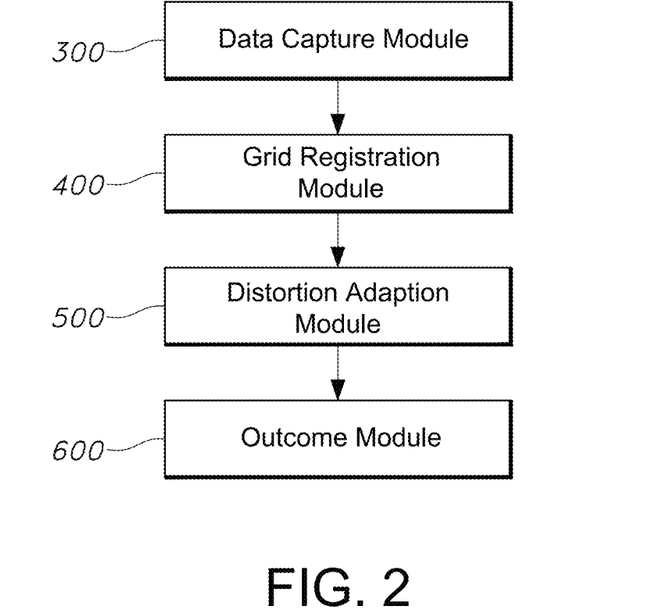
FIG. 2 shows a schematic overview of the software flow diagram of the system.

Turning to FIGS. 1 and 2, the application software 120 includes an image capturing module 300 that captures and stores the digital image acquired by an imaging device 220. In one embodiment, the image is in the DICOM image format. The acquired image is sent to the distortion calibration array registration module 400 for registration. The registered distortion calibration array is sent to the distortion adaptation module 500 for adaption of the dimensioned grid. At least one visual and/or auditory instruction is then sent to an outcome module 600. This module presents at least one instruction for the surgeon to adjust the implant placement and/or alignment until the surgeon is satisfied. The functionalities of these software modules will be discussed in detail below.

In one embodiment, the application software 120 is organized into modules and each module has at least one function block as shown in this figure. A hip alignment embodiment is used as an exemplary surgical procedure to illustrate the detailed operations of each block. It will be appreciated that the distortion calibration array based intraoperative system 100 disclosed here is not limited to perform only this surgical operation. For example, the present invention may be applicable to other musculoskeletal applications such as arthroplasty surgery for hip, knee, spine, ankle and shoulder as well as trauma surgery for musculoskeletal repair. It will be clear to one skilled in the art that the present invention may be practiced with variations of the specific details described hereinafter.

The application software 120 adapts the digital dimensioned grid patterns in real-time intra-operatively to fit the subject's anatomy, thus producing distorted patterns to match or fit the musculoskeletal anatomy or shape of the implant or trauma and producing at least one visual and/or auditory instruction or feedback intraoperatively to a user, such as a surgeon 202. The user 202 reviews the registered anatomical image with the distortion adjusted dimensioned grid. If adjustment of the patient or the diagnostic equipment is required, then the surgeon selects points on the patient anatomy, inputs the selected anatomical points into the work station, such as through the use of an input device 112, or in an alternate auto-segmentation can be selected by the surgeon. Once the points are inputted, they become pattern indicators for placement of the dimensioned grid.

Figure 3:
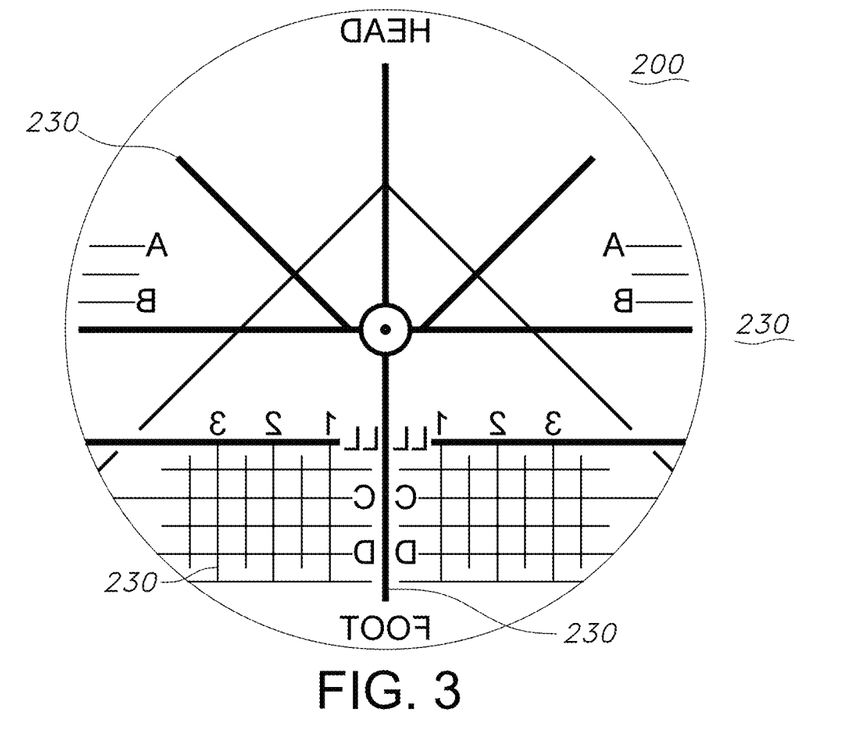
FIG. 3 shows an exemplary embodiment of a grid.

Now referring to FIG. 3, in an exemplary embodiment, a dimensioned grid 200 is shown. The dimensioned grid 200 can be either analogue or produced digitally. With respect to an embodiment of an analogue dimensioned grid 200, it has a plurality of dimensioned radio-opaque lines, e.g. 230 relating to surgical variables. The portion of the dimensioned grid 200 that is not opaque is radiolucent. The dimensioned grid 200 can include any shape or pattern of geometric nature or text to reference angles, length positioning or targeting. The dimensioned grid 200 can be a single line, a geometrical pattern, number, letter or a complex pattern of multiple lines and geometries that correspond to surgical variables. The grid patterns can be predesigned or constructed intra-operatively in real-time based upon the surgeon's knowledge of anatomy and clinical experience including interpretation of morphometric literature and studies identifying key relationships and dimensions between anatomical landmarks and its application in supporting good surgical technique as it relates to specific procedures. The analogue dimensioned grid 200 is used with an object being imaged intraoperatively with an imaging system 220, such as for example C-arm and flat plate. With respect to a digital dimensioned grid, this form of the dimensioned grid 200 is generated by the application software 120.

Figure 4:
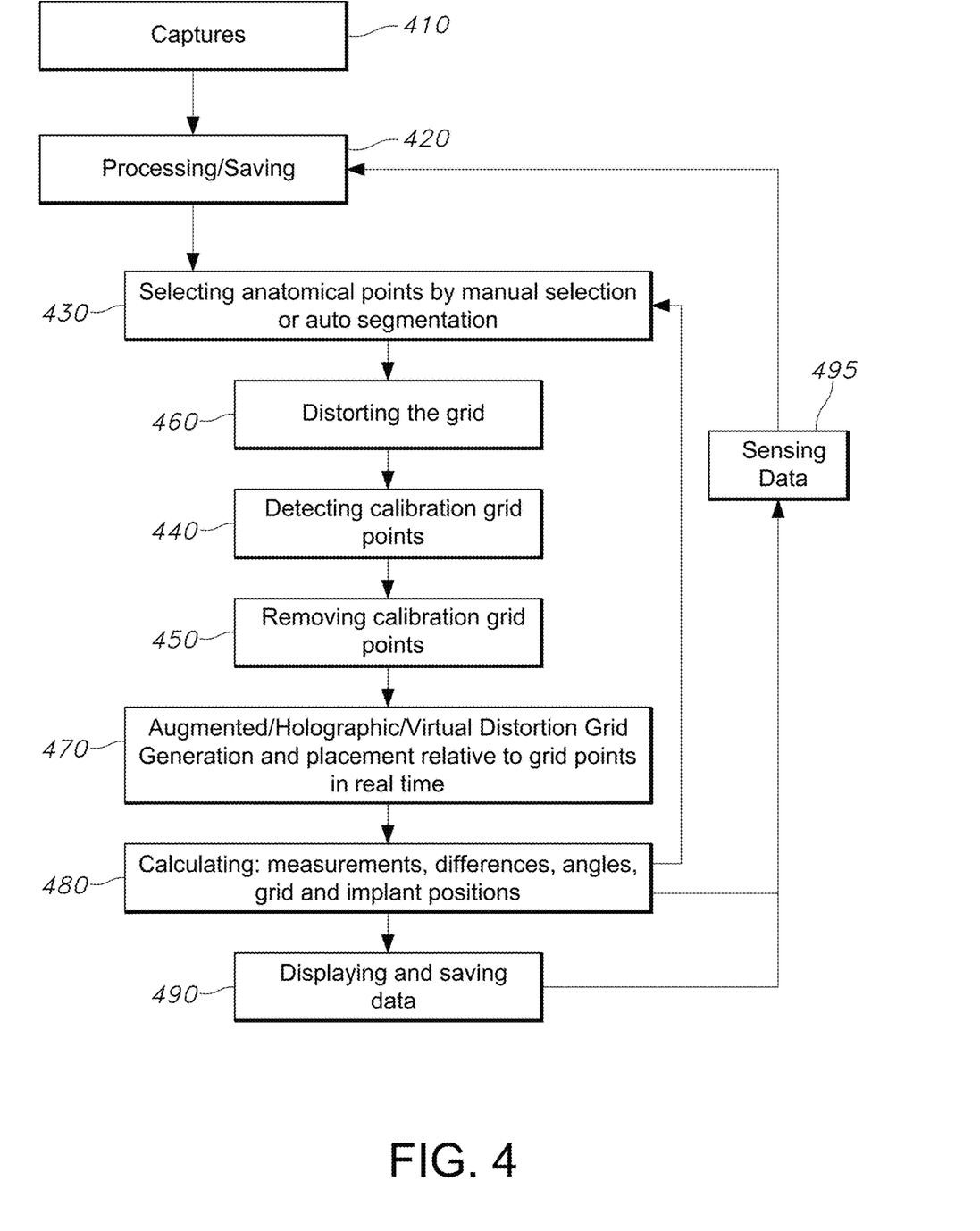
FIG. 4 shows an over-view schematic flow chart of the distortion correction method according to the present invention.

FIGS. 1 and 4 show a detailed flow diagram of the method of this invention. In the data capture module 300, a digital image is transmitted to a computer workstation 104 with a display to project the digital image. The digital image can be radiographic, MRI or an ultrasound image. The digital image is taken at the command of the surgeon or in one embodiment the digital image is continuously taken at a predefined interval during the entire operation.

The grid based intraoperative system 100 includes a display 114, such as a monitor screen, that is configured to display the digital image, other relevant text and graphic information to the surgeon. It can also be couple to an input device 112, such as keyboard, mouse, trackball or similar pointing devices, such as an infrared wand, as well as network communication peripherals (not shown) so that it can communicate with other external servers and computer. In an exemplary embodiment, grid or distortion calibration array based intraoperative system 100 receives DICOM images from an imaging system 220, such as a C-Arm, from the operative side and DICOM images of the contra lateral side of the patient. However, in some applications, such as surgery on a pelvis, only an x-ray image of one side is required. In this step of the process, an image of an anatomical portion of a patient is captured from Radiographic/CT/MRI/Ultrasound (Step 410) in real time intraoperatively or pre-operatively by a system that processes the image to provide an anatomical image model generation, saves the image and displays the image on a visualization screen (Step 420).

In the grid registration module 400, a user 202, such as a surgeon, selects at least one anatomical landmark 310 in the anatomical image on a visualization screen. The display is visually available for surgeon by viewing on a display medium such as a computer/tablet monitor, imaging system monitor, TV monitor, HUD, mixed reality glasses, augmented reality or holographic device such as glasses or contact lenses. The digital image can be 2D or a 3D generated shape model. Anatomical landmark 310 selection can be accomplished by a various methods including but not limited to: auto segmentation where the software uses feature/pattern recognition process to auto-detect known and targeted anatomical landmarks; use of remote infrared device, such as a gyro mouse; voice command; air gestures; gaze (surgeon uses gaze and direction of eye or head motion to control targeting or touching the visualization screen at the selected anatomical landmarks 310.

In one illustrative embodiment, the surgeon inputs the selection of the anatomical landmarks 310 to the workstation 104 manually or through the use of a variety of input devices 112 such as, an infrared wand or an augmented reality device. The application software registers a dimensioned grid 200 with the selected anatomical landmarks 310. The method includes the step of registering an anatomical image to a dimensioned grid by selecting at least one anatomical landmark 310 to provide a dimensioned grid with at least one grid indicator (Step 430).

In the distortion correction module 500, a registration procedure is used to compute the deformation of the digital grid indicators. The initial step in the registration process is calibration (Step 440). The software identifies and recognizes calibration points 520 that are radiopaque in the image. These are of known dimensioned geometries. A grouping of these points is a distortion calibration array 522. The distortion calibration array 522 is placed on the image intensifier 208 or in the field of view of any imaging system 220 so that the known distortion calibration array lines/points are identified when an image is taken and captured. These known patterns are saved for use in the distortion adaptation/correction process (Step 450). The distortion calibration array 522 is removed from visualization on the display medium in order to not obscure and clutter the image with unnecessary lines/points (Step 450).

Figure 5A:
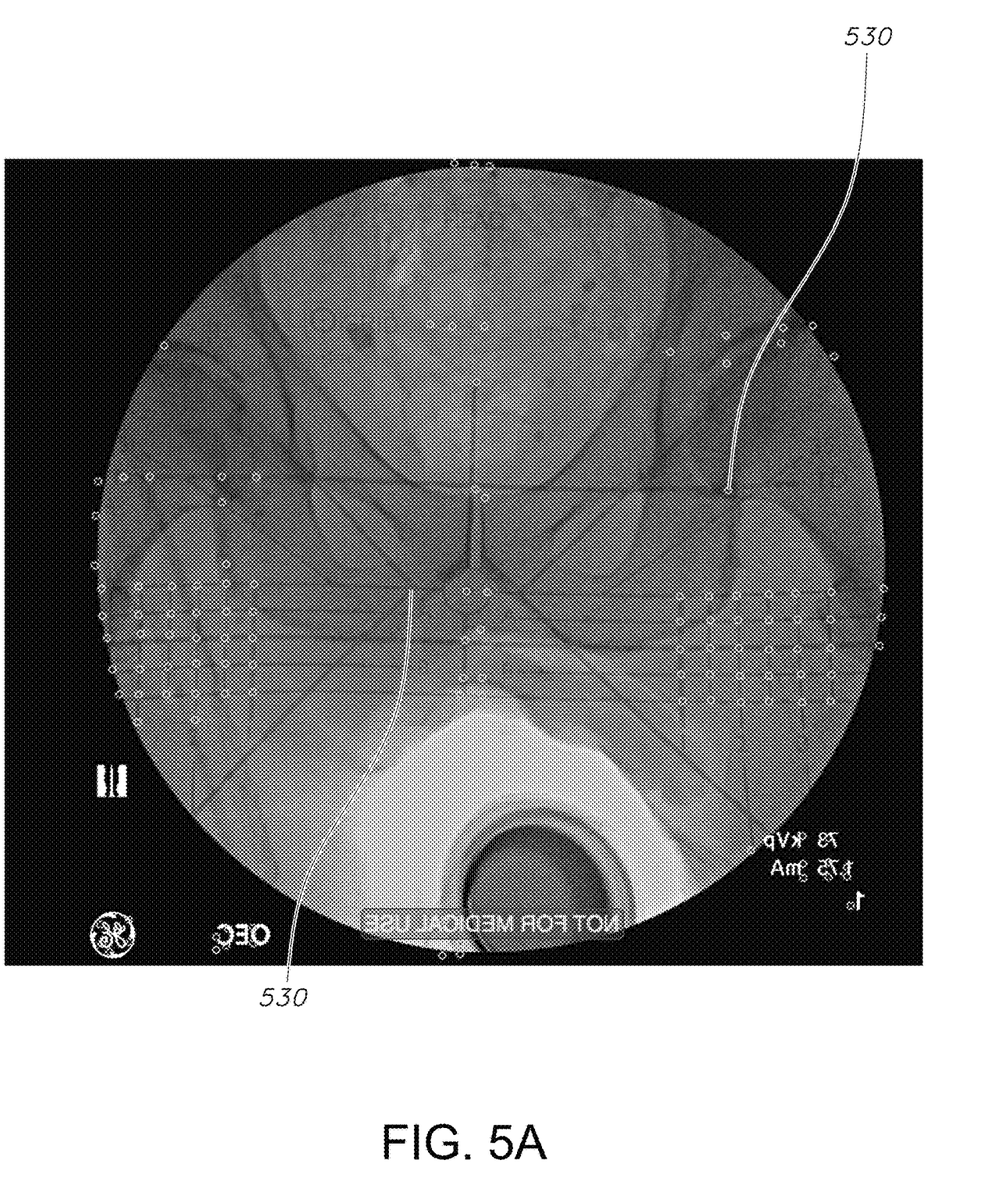
FIG. 5A is a screen shot image of a calibration grid and FIG. 5B is a screen shot image of a calibration grid.
Figure 5B:
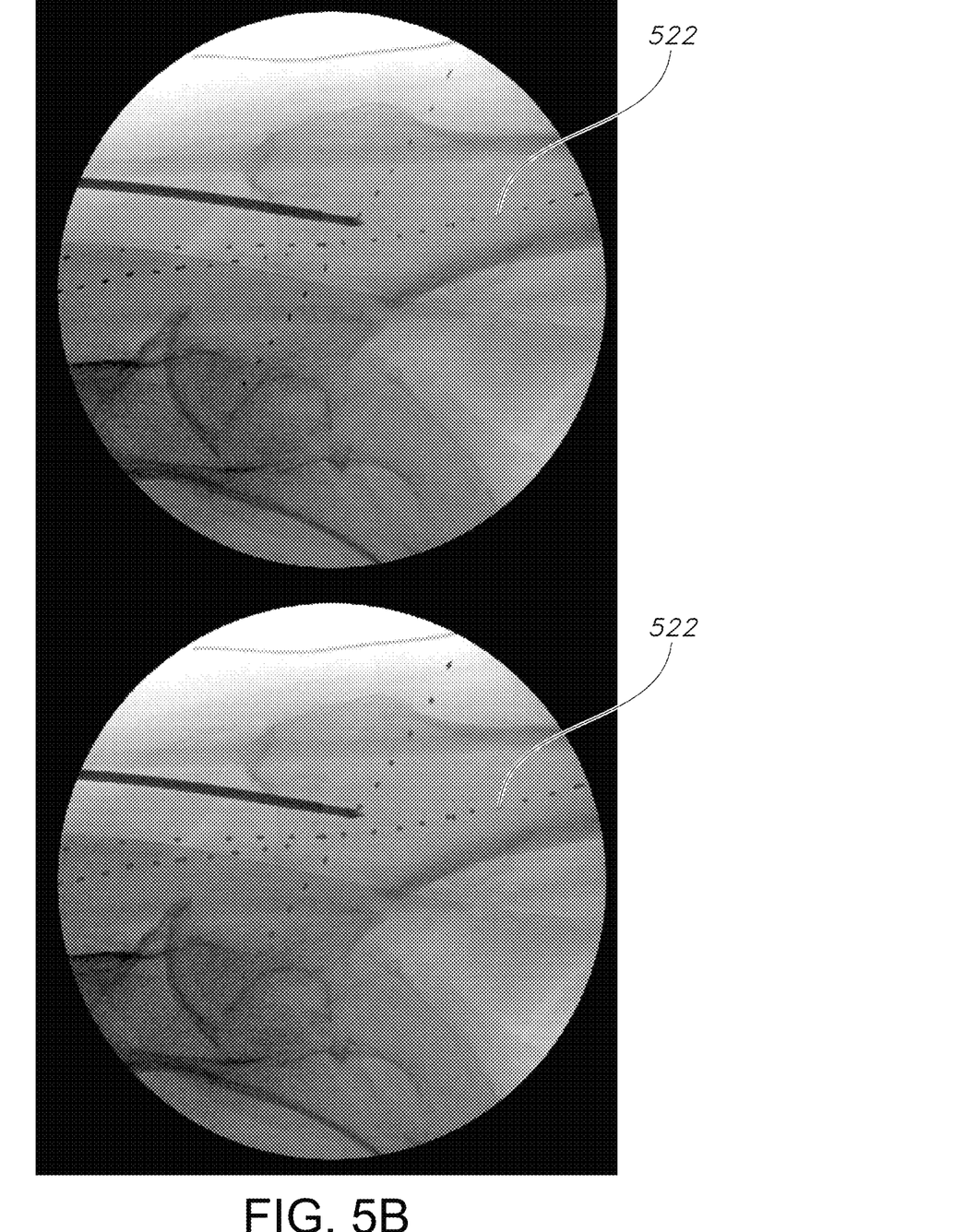

Now referring to FIGS. 5A and 5B, distortion calibration array 522 is shown. A distortion calibration array 522 in this illustrative embodiment is made a series of lines or points that are placed in order to support the distortion adaptation of the dimensioned grid 200. The distortion calibration array points or lines 520 are radiopaque so that the distortion process can calculate the location of these points/lines 522 relative to the anatomy and quantify the amount of distortion during each image taken. Once these points/lines are identified and used in the distortion process, there is another process that removes the visualization of these points/lines from the anatomical image so that they are not obstructing the surgeons view when the sees the dimensioned grid 200 and the anatomical image.

In one embodiment, the registration process involves manually or automatically detecting grid landmarks (such as grid line intersections, points, and line segments) on the dimensioned grid 200 superimposed on the anatomical image and then aligning those landmarks via an affine registration and a deformation field with corresponding landmarks on a distortion calibration array 522 of known geometry, which is a represented digitally. The method includes the step of deforming the calibrated dimensioned grid to correct for the distortion of the anatomical image to generate a deformed calibrated dimensioned grid image. Known radiopaque lines/points (from distortion calibration array 520) are used to provide a measure of EM distortion in each anatomical image. The distortion is quantified and then the software generated virtual grid is adapted to match the distorted anatomy in each anatomical image 240 (Step 460).

Figure 6:
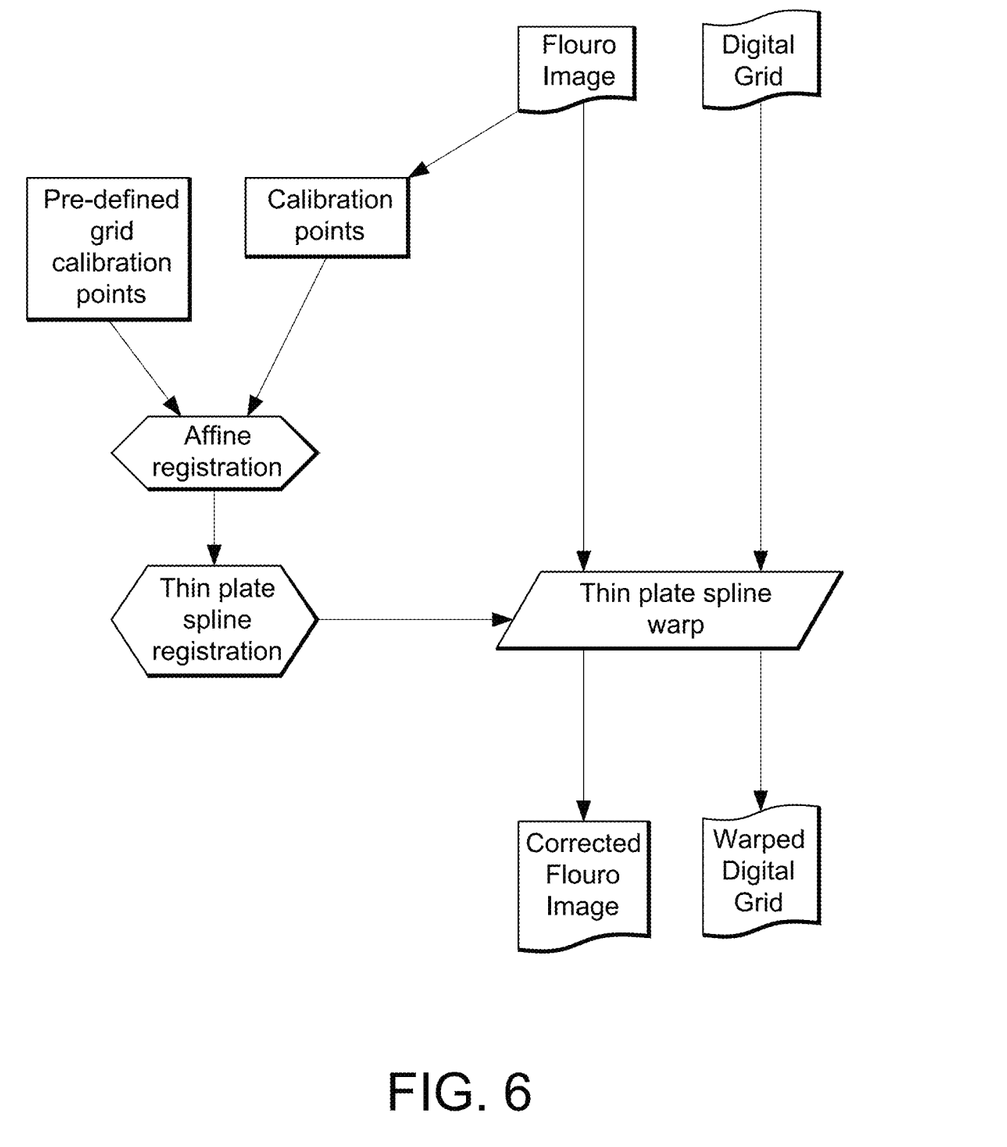
FIG. 6 shows a schematic overview of the distortion correction process.
Figure 7A:
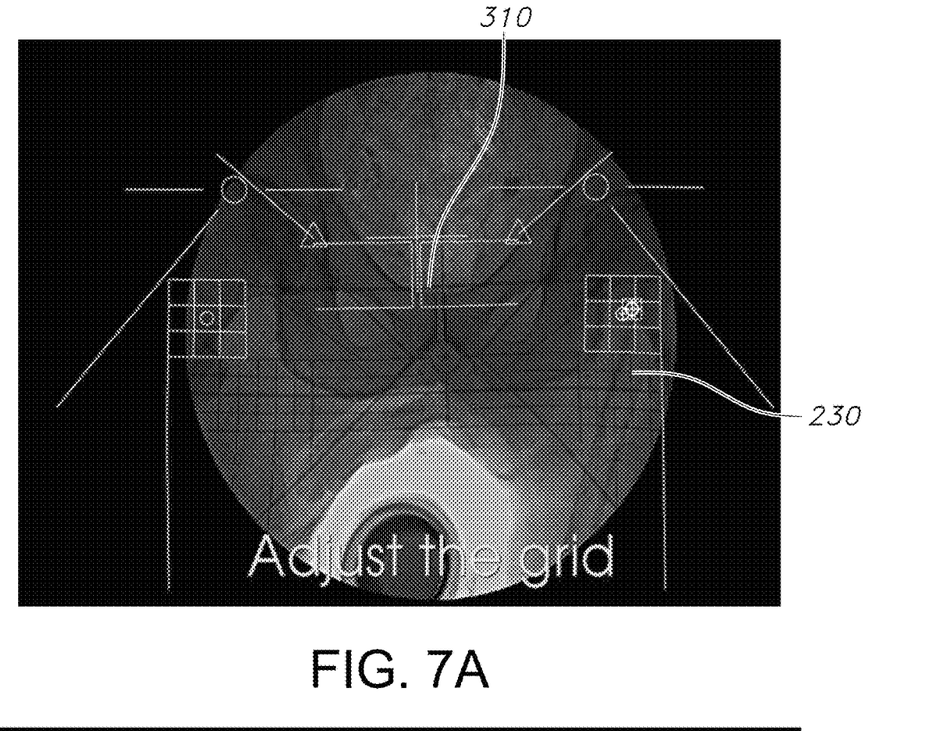
FIGS. 7A and 7B are screen shot images of the user view of the distortion correction step.
Figure 7B:
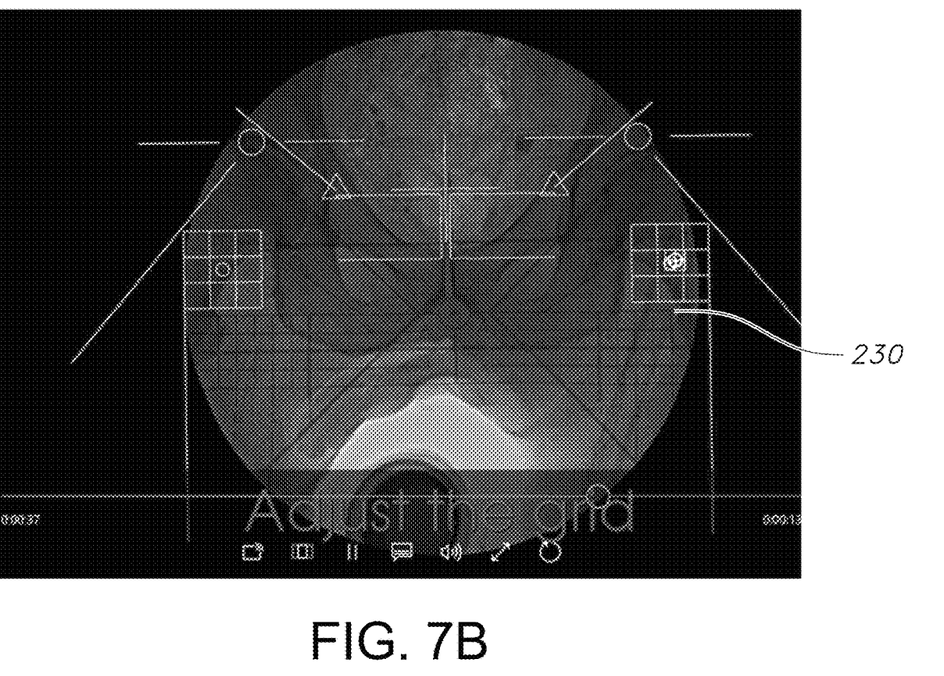

Now referring to FIGS. 6, 7A & 7B, the distortion calibration array 200 is of non-uniform design, such that the selected anatomical landmarks 310 are clustered more densely in regions of interest to the surgeon, in order that the deformation correction may be estimated with greater precision in those regions. The deformation estimation proceeds as follows: once selected anatomical landmarks 310 have been identified (either manually or automatically) on the array image, an Affine Transformation that produces the best mapping between corresponding selected anatomical landmarks 310 from the dimensioned grid 200 to the array image is computed. Following transformation of the grid points by the Affine Transformation, which adjusts the landmarks for translation, rotation, and scaling with respect to the array image landmarks in the Deformation Field (which is the residual difference between transformed grid points and the array image points) is modeled using Thin-Plate Splines or any other suitable radial basis functions. Parameters of the Thin-Plate Splines or radial basis functions are estimated by solving a linear system of equations.

Once the deformation field has been computed, the dimensioned grid is adapted in real-time intra-operatively to fit the patient anatomy, thus producing a distorted grid indicator, such as lines curving that can be used to match or fit the musculoskeletal anatomy or the shape of the implant. The deformation of the grid indicators is then applied in real-time by first applying the Affine Transformation and then warping the grid indicators along the Deformation Field. A grid pattern based upon the anatomical points that was defined and targeted in landmark identification is generated. The software program is configured to compute the amount of distortion in each image and it quantifies this amount relative to the anatomy/anatomy image and then displays the calculated grid/Image relationship. displaying an image of the patient's anatomy with the quantitatively distorted dimensioned grid image. These deformed grids are tracked in real time with each new image taken. The deformed grid can be positioned relative to anatomy, implant, and fractures auto or manually by the user such as a surgeon (Step 470).

Numerous equations and formulas are used within the algorithms to calculate: measurements, differences, angles, grid and implant positions, fracture deviations to determine at least one measurement of surgical variables involving the implant or trauma (Step 480). In the output module 500, at least one measurement of surgical variables involving the implant or trauma is presented to the user. This facilitates the placement of the implant or treatment of the trauma in the patient (Step 490). Once the preoperative plan is prepared and reviewed the surgeon positions the subject, such as a patient with respect to the radiographic system, such as an x-ray device. The surgeon obtains a radiographic image, such as an x-ray of an area of interest. In the first step of the method, the radiographic images are generated and transferred to the workstation with a display device. The anatomical image is displayed and surgeon reviews the radiographic image. Anatomical points are selected by the surgeon and then the grid is registered to the image using image registration based on the selected anatomical landmark points. Image registration is defined as an Affine Transformation of the grid to produce a best fit between predefined landmark points on the grid and their corresponding anatomical landmark points. Affine Transform parameters that produce a best fit may be defined as those parameters that produce the minimal least squares differences between predefined landmark points and anatomical landmark points, but may also include other optimization criteria. Following image registration, an estimation of the 3D pitch and yaw of the patient anatomy may be made using inter-anatomical landmark differences and an assumption of the symmetry of the anatomy of the patient.

Measurements and data can also be sent to or communicated with a robotic system, haptic controlled device or touch/force sensor to a mixed/augmented/holographic reality display showing visualization, alignment, and placement of instruments, bones or implants in 2D/3D mixed/augmented/holographic reality image/shape model with the dimensioned grid in a surgical environment in real-time intraoperatively by projecting mixed/augmented reality grid data and image measurements for live mixed/augmented reality tracking of the dimensioned grid, surgical instruments and implant (step 495).

Figure 8:
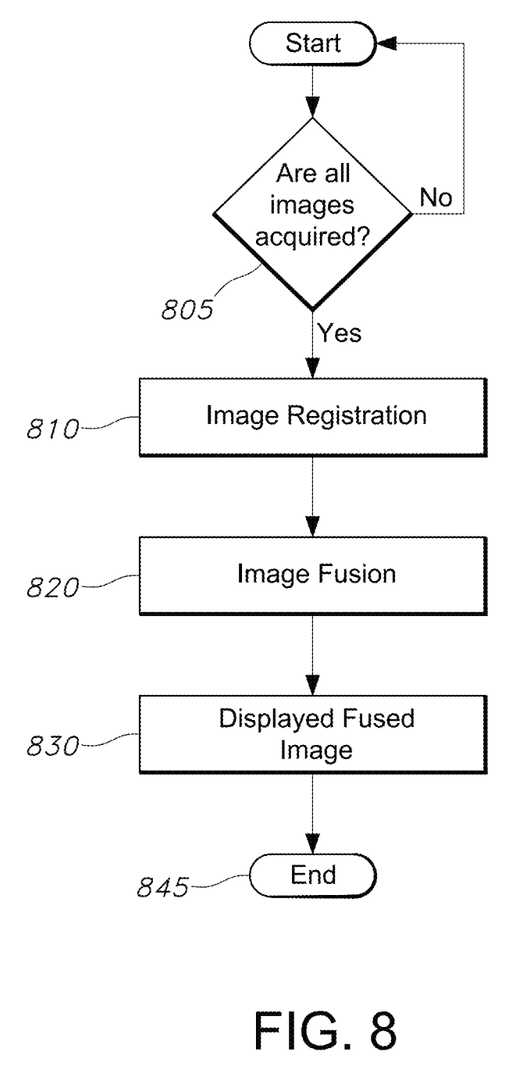
FIG. 8 shows an overview of the software flow diagram of the auto-segmentation process.
Figure 9:
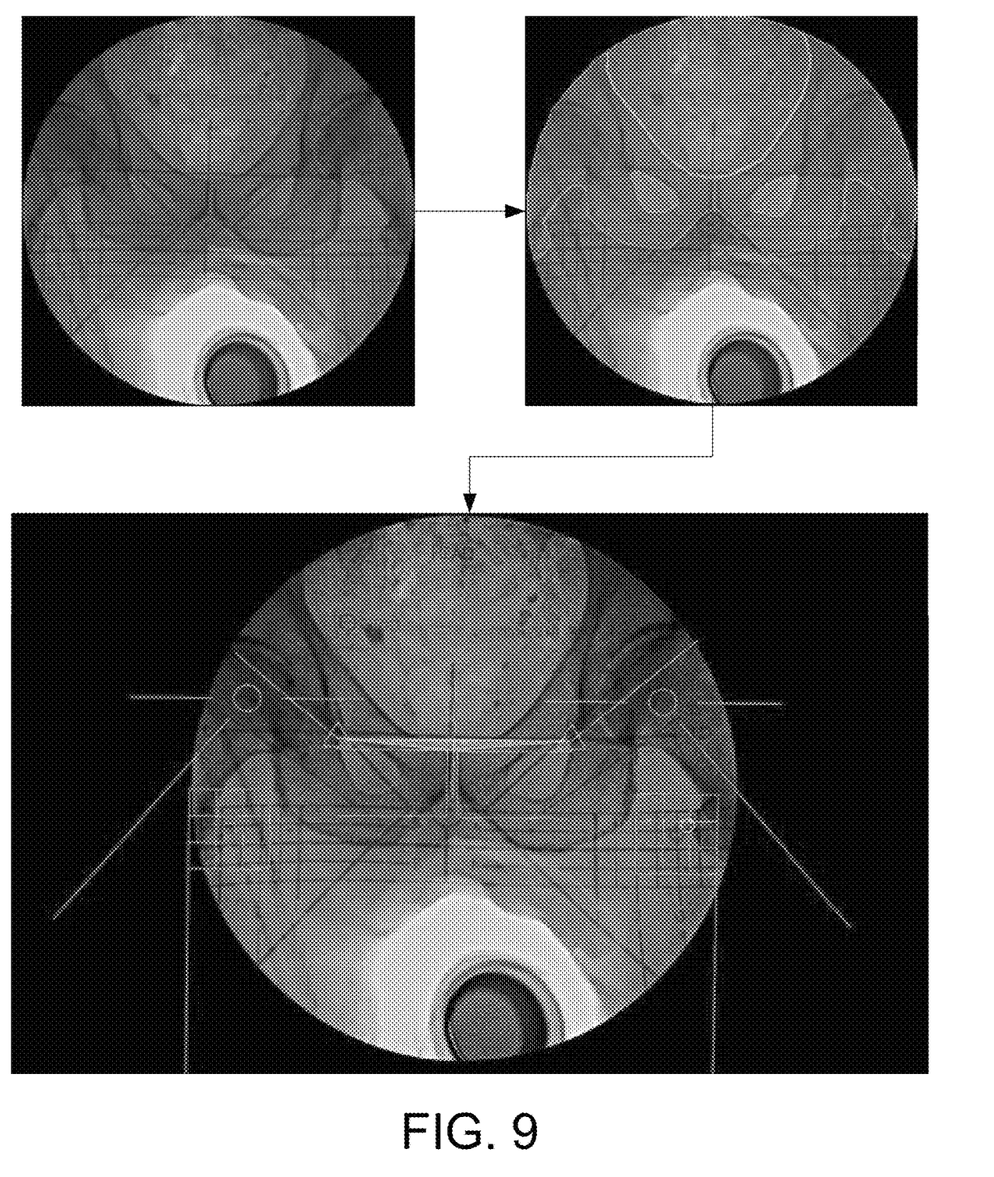
FIG. 9 shows exemplary view of a screen shot of the auto-segmentation process.

Now referring to FIGS. 8 and 9, the auto-segmentation module is shown. In auto-segmentation, the at least one anatomical landmark 310 selected by the surgeon is automatically selected for each successive anatomical image. Auto-segmentation allows a surgeon to work more rapidly. Auto-segmentation is accomplished through a combination of one or more of the following techniques: intensity thresholding; feature detection on the intensity edges in the image, including shape detection via the Hough Transform or other methods; feature detection followed by registration of a 2D or 3D anatomical atlas with predefined landmark positions. With respect to the system, in one embodiment, the application software 120 is organized into modules and each module has at least one function block as shown in this figure. Function 810 includes automatic segmentation, function 820 includes automatic grid point selection, function 830 involves create grid from selected points and function 840 involves an overlay of the grid on an anatomical image.

Figure 10:
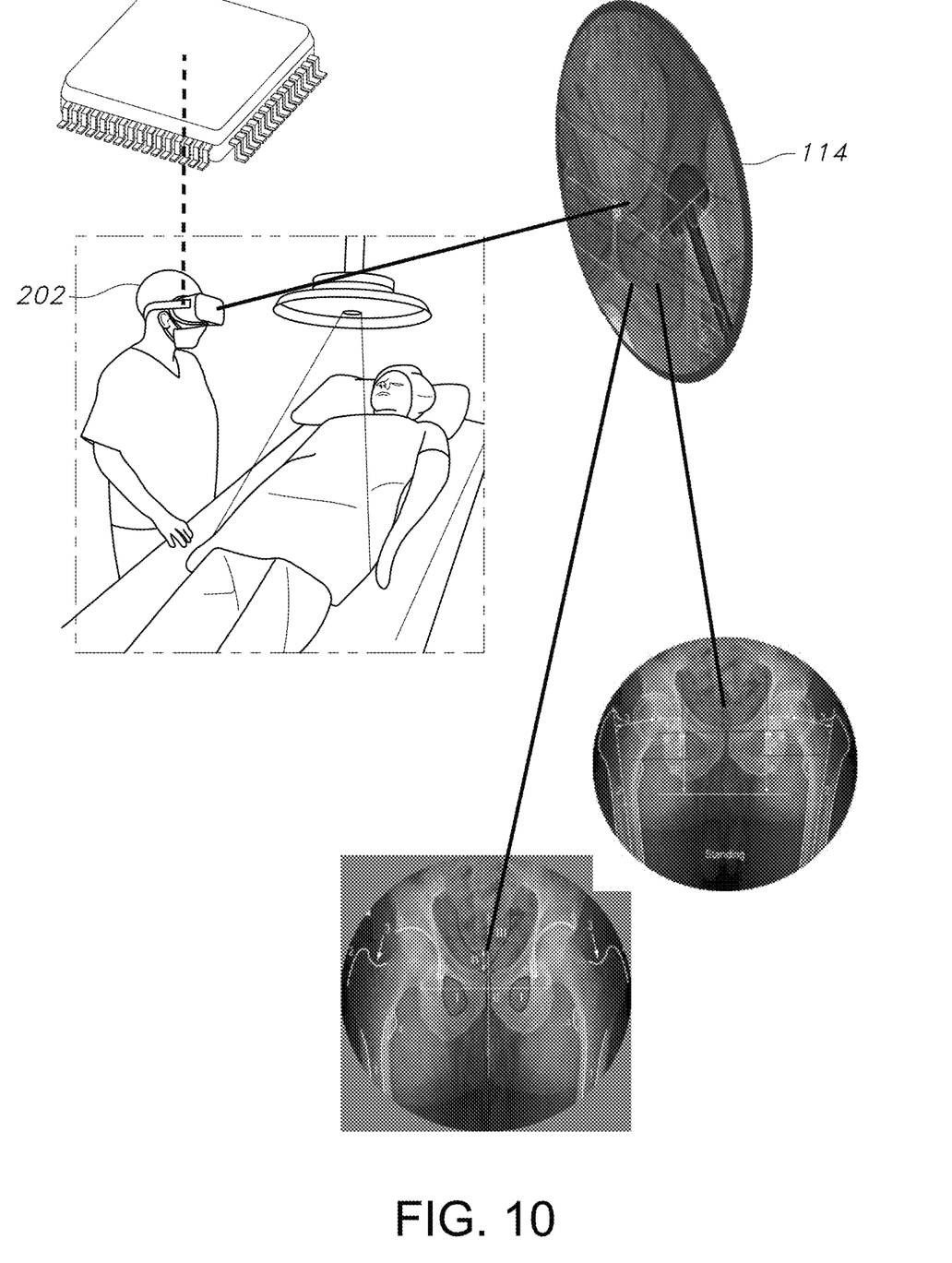
FIG. 10 shows an exemplary view of a head-up display view of the system.

Now referring to FIGS. 1 and 10, an alternative embodiment of the system 100 is shown. The system components include an input of a series of x-ray or fluoroscopic images of a selected surgical site, a system 100 to process the surgical images and an overlay of a virtual, augmented, or holographic dimensioned grid 200, with an input device 112 to provide manipulation of the dimensioned grid 200 by a user 202, such as a surgeon. In one embodiment, the electronic display 114 is an electronic display device, such as a computer monitor, or a heads-up display, such as Glass (Google). In another embodiment, the electronic display screen 114 is a video fpv goggle. An out-put to an electronic display 114 is provided for the user 202 to view the overlay of the series of images and the dimensioned grid 200. The augmented reality or holographic dimensioned grid 200 can be manipulated by the user 202 by looking at anatomic landmarks, the shown on the electronic display 114 that will facilitate locking on the correct alignment/placement of surgical device. The system 100 allows the user 202 to see critical work information right in their field-of-view using a see-through visual display and then interact with it using familiar gestures, voice commands, and motion tracking. The data can be stored in data storage 110. Applications include hip, knee, shoulder, elbow, and ankle arthroplasty, trauma fractures and limb deformity correction, spine, and sports medicine procedures such as femoroacetabular impngement/PAO.

While the invention has been described with reference to preferred and example embodiments, it will be understood by those skilled in the art that a variety of modifications, additions and deletions are within the scope of the invention, as defined by the following claims.

The invention claimed is:

1. A computer-implemented method, performed by a processor configured by a readable program code to perform the method, comprising the steps of:

capturing an image acquired by an imaging device of a patient's anatomy;

registering the image of the patient's anatomy to a dimensioned digital grid by selecting an at least one anatomical landmark to provide a dimensioned digital grid with at least one grid indicator; wherein the digital dimensioned grid is selected from the group consisting of a line, a geometrical pattern, a number, a letter and a complex pattern of multiple lines and geometries corresponding to a surgical variable configured to be superimposed on an intra-operative image anatomical image;

providing a calibration array selected from the group consisting of a line and a shape matching an anatomical feature;

calibrating the dimensioned digital grid to the image of a patient's anatomy to provide a calibrated dimensioned digital grid;

deforming the calibrated dimensioned digital grid to correct for the distortion of the patient's anatomy to generate a deformed calibrated dimensioned digital grid image; and     displaying the registered image with reference to the deformed calibrated dimensioned digital grid image.

2. The method of claim 1 wherein the step of calibrating the dimensioned digital grid comprises calculating the location of the calibration array relative to the anatomy of the patient and quantifying the amount of distortion in the image.

3. The method of claim 1 wherein a deformation field is computed from the at least one anatomical landmark using a thin-plate spline.

4. The method of claim 3 wherein the step of registering the intra-operative image further comprises: aligning the at least one anatomical landmark of the dimensioned digital grid with an at least one anatomical landmark in a distortion calibration array image using an affine transformation and the deformation field.

5. The method of claim 1 further comprising the steps of if the surgeon elects to adjust a patient or an equipment, selecting a point on the anatomy of the patient to direct the placement of the dimensioned digital grid.

6. A digital grid distortion calibration array based intra-operative system comprising: a non-transitory computer-readable storage medium encoded with computer-readable instructions which form the application software and a processor to process the instructions, wherein the application software includes:

a data capture module configured to capture and store a digital radiographic image of a patient acquired intra-operatively by an imaging device;

a grid registration module configured to register an anatomical image from said digital radiographic image of a patient with a digital grid and calibrate a digital representation of the digital grid to the image a patient's anatomy to provide a calibrated digital grid, said grid registration module comprising a calibration array selected from the group consisting of a line and a shape matching an anatomical feature and a digital dimensioned grid selected from the group consisting of a line, a geometrical pattern, a number, a letter and a complex pattern of multiple lines and geometries corresponding to a surgical variable configured to be superimposed on an intra-operative anatomical image, wherein the deformed digital dimensioned grid matches a quantitative warp amount within an intra operative anatomical image;

a distortion adaptation module configured to deform the digital representation of the digital grid to correct for distortion in the anatomical image; and an outcome module configured to provide at least one intraoperatively instruction to a user and intraoperatively displaying the anatomical image of the patient's anatomy with reference to the deformed calibrated digital grid image.

7. The system of claim 6 further comprising: an auto-segmentation module configured to automatically select for a successive anatomical image for an at least one anatomical landmark.

8. The system of claim 6 wherein said outcome module comprises a digital grid selected from the group consisting of: mixed, augmented reality, and holographic grid.

9. The system of claim 6 wherein said data capture module is configured to obtain data from a sensor.

10. The system of claim 9 wherein said sensor is in electronic communication with a grid selected from the group consisting of: a mixed reality, an augmented reality, and a holographic grid.

11. The system of claim 9 wherein said outcome module comprises a display selected from the group consisting of: a mixed reality display, an augmented reality display and a holographic display.

* * * * *